United States Patent [19]

Décor

[11] 4,110,538
[45] Aug. 29, 1978

[54] PROCESS FOR THE PREPARATION OF ACETAL SULPHONES

[75] Inventor: Jean-Pierre Décor, Thurins, France

[73] Assignee: Rhone-Poulenc Industries, Paris, France

[21] Appl. No.: 771,815

[22] Filed: Feb. 23, 1977

[30] Foreign Application Priority Data

Feb. 25, 1976 [FR] France ............... 76 05244

[51] Int. Cl.$^2$ ............................................. C07C 147/06
[52] U.S. Cl. ............................ 560/11; 260/607 AR; 260/607 AL; 260/609 F
[58] Field of Search .............. 260/607 AR, 607 AL, 260/470, 600 F; 560/11

[56] References Cited

U.S. PATENT DOCUMENTS

| | | | |
|---|---|---|---|
| 3,781,313 | 12/1973 | Julia | 260/607 AR |
| 3,803,252 | 4/1974 | Chabardes | 260/607 AL |
| 3,848,000 | 11/1974 | Chabardes | 260/607 AL |
| 3,850,991 | 11/1974 | Chabardes | 260/607 AL |
| 3,865,878 | 2/1975 | Chabardes | 260/607 AL |
| 3,906,967 | 6/1976 | Olson | 260/607 AR |

*Primary Examiner*—James O. Thomas, Jr.
*Assistant Examiner*—Michael Shippen
*Attorney, Agent, or Firm*—Stevens, Davis, Miller & Mosher

[57] ABSTRACT

Acetal sulphones useful as intermediates in the preparation of vitamin A and other terpene compounds are made by reacting a sulphone of the formula:

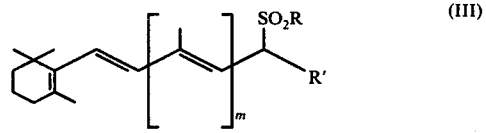

(III)

with an ω-halogeno-acetal of an ethylenically unsaturated aldehyde of the formula:

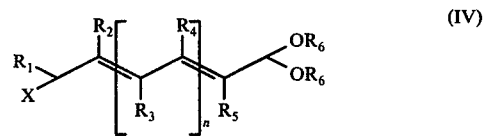

(IV)

in which $m$ and $n$ each represent zero or 1 and are such that $m+n=1$, $R_1$, $R_2$, $R_3$, $R_4$ and $R_5$, which may be identical or different, represent hydrogen or straight or branched alkyl radical of 1 to 6 carbon atoms, $R_6$ represents straight or branched alkyl of 1 to 6 carbon atoms, R represents straight or branched alkyl of 1 to 6 carbon atoms or arylalkyl containing a straight or branched alkyl of from 1 to 6 carbon atoms or aryl, unsubstituted or substituted by alkyl, alkoxy, alkylthio, alkoxycarbonyl, hydroxyl or halogen, and R' represents hydrogen or, if $m$ is zero, straight or branched alkyl of 1 to 6 carbon atoms.

3 Claims, No Drawings

PROCESS FOR THE PREPARATION OF ACETAL SULPHONES

The present invention provides a process for the preparation of sulphones of the formula:

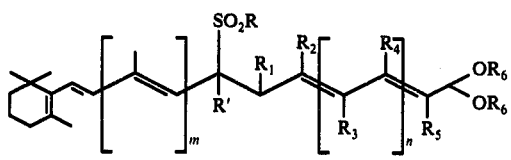

in which m and n represent zero or 1 and are such that the sum of $m+n=1$, $R_1$, $R_2$, $R_3$, $R_4$ and $R_5$, which may be identical or different, represent hydrogen or straight or branched alkyl of 1 to 6 carbon atoms, especially methyl or ethyl, $R_6$ represents straight or branched alkyl of 1 to 6 carbon atoms, especially methyl or ethyl, R represents straight or branched alkyl of 1 to 6 carbon atoms, or arylalkyl containing a straight or unbranched alkyl of from 1 to 6 carbon atoms or aryl (such as phenyl), the aryl or the aryl moiety of the arylalkyl being unsubstituted or substituted by straight or branched alkyl preferably of from 1 to 6 carbon atoms, straight or branched alkoxy preferably of from 1 to 6 carbon atoms, straight or branched alkylthio preferably of from 1 to 6 carbon atoms, straight or branched alkoxycarbonyl such that the alkoxy is preferably of from 1 to 6 carbon atoms, hydroxyl or halogen, R' represents hydrogen or, if m is zero, straight or branched alkyl of 1 to 6 carbon atoms, especially methyl or ethyl.

The compounds of formula I are useful as intermediates in the preparation of the corresponding ethylenically unsaturated aldehydes of the formula:

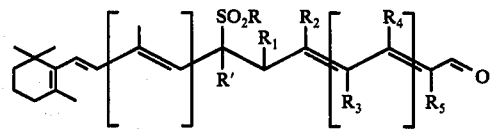

in which the symbols are as defined above.

The products of the formula (I) are known and described in particular in Belgian Pat. Nos. 794,872 and 807,036. According to these patents, the products of the general formula (I) are prepared by the action of a sulphone of the formula:

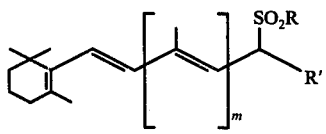

in which R and R' are defined as above and m is zero or 1, on an ω-halogeno-acetal of an ethylenically unsaturated aldehyde of the formula

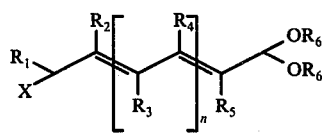

in which $R_1$, $R_2$, $R_3$, $R_4$, $R_5$ and $R_6$ are as defined above, X represents a halogen atom and n is zero or 1 depending on the meaning of the symbol m in the product of the formula (III) used.

These processes have the disadvantage of requiring the products of the general formula (IV) as starting materials, since these products are accessible only with difficulty. The γ-halogeno-acetals of ethylenically α,β-unsaturated aldehydes can be prepared by halogenoalkoxylation of 1-alkoxy-1,3-dienes with N-halogenosuccinimide in the presence of an alcohol, in accordance with the process described by S. M. MAKIN et al., J. Gen. Chem. USSR, 32 1088 (1962). This access route has the disadvantage of the difficulty of preparation of the starting ethylenically di-unsaturated ethers, which are themselves prepared by treating acetals of ethylenically α,β-unsaturated or β,γ-unsaturated aldehydes at high temperature in the presence of catalysts, the starting materials themselves being difficult to synthesize. Although the method of MAKIN can also be applied to the synthesis of ω-halogeno-acetals of aldehydes containing a system of conjugated double bonds, the preparation of such products by this method presents very great problems because of the difficulty of access to the necessary starting materials.

It has now been found that products of the general formula (I) can be prepared in excellent yield using starting materials which are easily accessible. The process of the invention comprises reacting a sulphone of the formula (III) with an α-halogeno-acetal of an ethylenically unsaturated aldehyde of the formula:

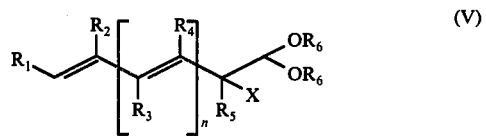

in which $R_1$, $R_2$, $R_3$, $R_4$, $R_5$, $R_6$ and X are as defined above and n is equal to zero or 1, depending on the meaning of the symbol m in the starting material of formula (III) used, such that $m+n=1$.

The reaction is preferably carried out in a basic polar aprotic solvent and in the presence of a basic agent having sufficient activity to anionise the sulphone employed. Dimethylformamide, dimethylacetamide, dimethylsulphoxide, N-methylpyrrolidone and hexamethylphosphotriamide are particularly suitable as basic polar aprotic solvents. The basic agents which are suitable may be inorganic or organic compounds: alkali metal alcoholates, alkali metal hydrides or amides, and organo-metallic compounds such as organo-zinc, organo-lithium and organomagnesium compounds are, for example, suitable. They may be used alone or jointly with another basic agent intended to neutralise the hydracid formed. In the case where the anion-forming agent is used alone, the quantity employed must be sufficient to ensure this neutralisation. This quantity is also dependent on the circumstances of use and on the reactivity of the products of the reaction with respect to this basic agent. For these various reasons, it can be advantageous to introduce a lesser quantity of anion-forming agent into the reaction mixture and to add another basic agent, with respect to which the products of the reaction are less sensitive and which is sufficient to neutralise the hydracid formed.

The reaction can take place at temperatures of between −100° and +150° C, depending on the nature of the starting materials and products, and preferably under an inert atmosphere, for example under argon.

The starting materials of the formula (V) can be prepared by the action of a hypohalite of a saturated aliphatic tertiary alcohol on an aldehyde of the formula:

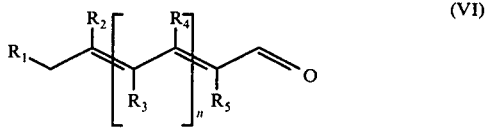

in which $R_1$, $R_2$, $R_3$, $R_4$ and $R_5$ are as defined above and $n$ is equal to zero or 1, in the presence of a saturated aliphatic primary alcohol of the general formula $R_6OH$ in which $R_6$ is as defined above.

The hypohalite of a saturated aliphatic tertiary alcohol used is preferably a bromine or chlorine derivative. The hypohalite of tert.-butanol is preferred for reasons of ease of availability. However, the hypohalites of higher alcohols containing up to 13 carbon atoms are also suitable. Generally, the hypohalite is used as a solution in an organic solvent which is inert under the reaction conditions, such as a liquid lower aliphatic hydrocarbon, for example pentane, an aromatic hydrocarbon, for example benzene, toluene or a xylene, or a halogenated aliphatic or aromatic hydrocarbon.

The temperature of the reaction is not critical and can, for example, be between $-40°$ and $+80°$ C. Preferably, the reaction is carried out at a temperature less than $0°$ C, for example at about $-20°$ C, in order to avoid appreciable decomposition of the reagent.

Generally, the quantities of the hypohalite and of the aldehyde of the formula (VI) are close to the stoichiometric quantities, but an excess of one or other of these reagents can be used without disadvantage. Generally, it is sufficient to use a stoichiometric quantity of the alcohol of the formula $R_6OH$; but it is preferable to use an excess of this reagent which thus serves as the reaction medium.

In order to speed up the reaction rate, it is advantageous to carry out the reaction in the presence of a catalytic quantity of a strong inorganic acid known as a catalyst for acetal formation, such as hydrochloric acid or sulphuric acid. This acid may be introduced into the reaction mixture at the start of the reaction, or only after the reaction of the hypohalite with the aldehyde of the formula (VI).

The compounds of formula (V) and their preparation are described and claimed in my application Ser. No. 771,304, entitled "Alpha-halogeno-acetals of Ethylenically unsaturated aldehydes and their Preparation", filed on even date herewith.

The sulphones of the formula (III) are known; their preparation is in particular described in Belgian Pat. Nos. 794,872 and 807,036.

The monoene and diene aldehydes of the formula (VI) are known or can be prepared by applying known methods.

The compounds of the formula (I) can be used as starting materials for the preparation of polyene compounds of the terpene, geraniolene and sesquiterpene series. Desulphonation of the compounds of the formula (I) by treatment with an inorganic or organic basic agent allows a further ethylenic double bond to be introduced into the aliphatic chain as described in Belgian Pat. Nos. 794,872 and 807,036.

The process for the preparation of the products of the formula (I) according to the present invention is of very particular interest for the preparation of the compounds of the formula (I) in which: $m$ is 1, $n$ is zero, $R'$, $R_1$, $R_3$, $R_4$ and $R_5$ each represent hydrogen and $R_2$ represents methyl, or $m$ is zero, $n$ is 1, $R_1$, $R_2$, $R_3$ and $R_5$ each represent hydrogen and $R'$ and $R_4$ each methyl, which are precursors for vitamin A.

The compounds of the formula (I) obtained by the process described above are useful in the preparation of the corresponding aldehydes of the general formula (II). The de-acetalisation of a compound of formula (I) can be carried out by any method which is in itself known for the de-acetalisation of analogous compounds. Generally, the de-acetalisation is carried out by the action of an excess of water, at a pH equal to or lower than 7 and at a temperature of between $-40°$ and $+80°$ C, and preferably between $-20°$ and $+40°$ C.

Generally, it is not necessary to isolate the acetal sulphone of the formula (I) in order to de-acetalise it to the corresponding aldehyde. This conversion can generally be carried out on the crude product of the reaction between a sulphone of the formula (III) and the $\alpha$-halogeno-acetal of the formula (V).

The following Example illustrates the invention.

EXAMPLE

A solution of 3.44 g of phenyl 5-(2,6,6-trimethyl-1-cyclohexenyl)-3-methyl-2,4-pentadienyl sulphone of 94% purity ($1.1 \times 10^{-2}$ mols) in 5.74 cm$^3$ of N-methylpyrrolidone is added at $-20°$ C, under an atmosphere of argon and over a period of 5 minutes, to a mixture of 1.055 g ($1.1 \times 10^{-2}$ mols) of sodium tert.-butylate in 4.95 cm$^3$ of N-methylpyrrolidone. After stirring for 5 minutes at $-20°$ C, a solution of 2.368 g (1.135 mols) of 2-bromo-1,1-dimethoxy-3-methyl-3-butene in 4.5 cm$^3$ of N-methylpyrrolidone is added over a period of 1 hour. The reaction mixture is then stirred at $0°$ C for 2¼ hours, and then 12 cm$^3$ of diisopropyl ether, from which the peroxide has been removed, and 25 cm$^3$ of water are added to it over a period of 10 minutes. The aqueous phase is extracted twice with a total of 20 cm$^3$ of diisopropyl ether. The organic phases are combined. A solution of 1,1-dimethoxy-3,7-diemthyl-9-(2,6,6-trimethyl-1-cyclohexenyl)-2,6,8-nonatrienyl-5-phenylsulphone is obtained which can be converted directly to the corresponding aldehyde by carrying out the reaction in the following way.

The above solution is stirred at about $20°$ C for 1¾ hours with 0.247 cm$^3$ of a 4N aqueous sulphuric acid solution, then washed successively with 5 cm$^3$ of a saturated aqueous sodium bicarbonate solution and twice with a total of 5 cm$^3$ of water, and finally dried over anhydrous sodium sulphate. After filtering and cooling at $0°$ C for 15 minutes, 0.6275 g of 3,7-dimethyl-9-(2,6,6-trimethyl-1-cyclohexenyl)-1-oxo-2,6,8-nonatrienyl-5-phenylsulphone, identified by nuclear magnetic resonance spectrography, is filtered off.

By concentrating the mother liquors of the above product, a residue weighing 3.970 g is obtained which contains as measured by nuclear magnetic resonance, $8.122 \times 10^{-3}$ mols of 3,7-dimethyl-9-(2,6,6-trimethyl-1-cyclohexenyl)-1-oxo-2,6,8-nontrienyl-5-phenylsulphone and $0.53 \times 10^{-3}$ mol of the starting phenyl 5-(2,6,6-trimethyl-1-cyclohexenyl)-3-methyl-2,4-pentadienyl sulphone. The yield of the aldehyde sulphone is 91% based on the starting sulphone consumed.

The startng 2-bromo-1,1-dimethoxy-3-methyl-3-butene can be prepared in the following way. 1.6 cm³ of concentrated sulphuric acid are added to a solution of 5.04 g (6 × 10⁻² mols) of 3methyl-2-butenal (otherwise called prenal) in 50 cm³ of methanol, cooled to −20° C, followed by the addition, over a period of 90 minutes, of 77.5 cm³ of a 0.774 molar solution of tert.-butyl hypobromite in pentane. The temperature is then allowed to rise to 0° C over a period of 30 minutes. The reaction mixture is poured into 100 cm³ of water containing 11.16 g (0.9 × 10⁻² mol) of sodium bicarbonate. The aqueous phase is separated and extracted 3 times with a total of 75 cm³ of pentane. The organic phases are combined, washed with 30 cm³ of water and then with 30 cm³ of saturated aqueous sodium bicarbonate solution and dried over anhydrous sodium carbonate. After concentrating to dryness under reduced pressure (about 20 mm of mercury) at a temperature below 50° C, a residue of 12.92 g is obtained which consists of mixture of 2-bromo-1,1-dimethoxy-3-methyl-3-butene and 2-bromo-1,1,3-trimethoxy-3-methyl-butane, which are identified by nuclear magnetic resonance. 6.55 g of 2-bromo-1,1-dimethoxy-3-methyl-3-butene, b.p. 48.5° C 0.2 mm.Hg., are isolated by distillation.

The solution of tert.-butyl hypobromite in pentane can be prepared by the method described by C. WALLING J. Org. Chem., 27, 2976 (1962).

I claim:

1. Process for the preparation of a sulphone of the formula:

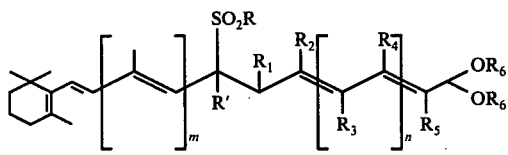

in which $m$ and $n$ each represent zero or 1 and are such that $m + n = 1$, $R_1$, $R_2$, $R_3$, $R_4$ and $R_5$, which may be identical or different, represent hydrogen or straight or branched alkyl radical of 1 to 6 carbon atoms, $R_6$ represents straight or branched alkyl of 1 to 6 carbon atoms, R represents straight or branched alkyl of 1 to 6 carbon atoms or arylalkyl containing a straight or branched alkyl of from 1 to 6 carbon atoms or aryl, the aryl or the aryl moiety of the aralkyl being unsubstituted or substituted by alkyl, alkoxy, alkylthio, alkoxycarbonyl, hydroxyl or halogen, and R' represents hydrogen or, if $m$ is zero, straight or branched alkyl of 1 to 6 carbon atoms, which comprises reacting a sulphone of the formula:

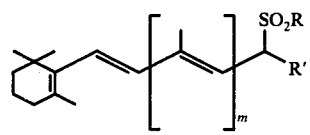

in which R and R' are as defined above and $m$ is zero or 1, in a basic polar aprotic solvent and in the presence of a basic agent having sufficient activity to anionise the said sulphone, with an α-halogeno-acetal of an ethylenically unsaturated aldehyde of the formula:

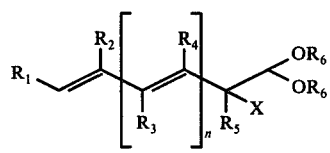

in which $R_1$, $R_2$, $R_3$, $R_4$, $R_5$ and $R_6$ are as defined above, and $n$ is zero or 1 and such that $m + n = 1$.

2. Process according to claim 1, in which the reaction is carried out at between −100° and +150° C.

3. Process according to claim 1, in which $m$ is 1, $n$ is zero, R', $R_1$, $R_3$, $R_4$ and $R_5$ are hydrogen, and $R_2$ is methyl, or $m$ is zero, $n$ is 1, $R_1$, $R_2$, $R_3$ and $R_5$ are hydrogen, and R' and $R_4$ are methyl.

* * * * *